(12) United States Patent
Lacroix

(10) Patent No.: US 6,830,887 B2
(45) Date of Patent: Dec. 14, 2004

(54) METHOD AND KIT FOR QUANTITATION AND NUCLEIC ACID SEQUENCING OF NUCLEIC ACID ANALYTES IN A SAMPLE

(75) Inventor: Jean-Michel Lacroix, Etobicoke (CA)

(73) Assignee: Bayer HealthCare LLC, Tarrytown, NY (US)

(*) Notice: Subject to any disclaimer, the term of this patent is extended or adjusted under 35 U.S.C. 154(b) by 245 days.

(21) Appl. No.: 10/082,546

(22) Filed: Feb. 25, 2002

(65) Prior Publication Data

US 2003/0165868 A1 Sep. 4, 2003

Related U.S. Application Data

(63) Continuation-in-part of application No. 09/818,182, filed on Mar. 27, 2001, now Pat. No. 6,653,107, which is a continuation of application No. 09/418,720, filed on Oct. 15, 1999, now Pat. No. 6,265,152, which is a continuation-in-part of application No. 08/938,641, filed on Sep. 26, 1997, now Pat. No. 6,007,983, and a continuation-in-part of application No. 08/819,912, filed on Mar. 18, 1997, now Pat. No. 5,795,722.

(51) Int. Cl.$^7$ .......................... C12Q 1/68; C12P 19/34; C07H 21/04
(52) U.S. Cl. ........................ 435/6; 435/91.2; 536/23.1
(58) Field of Search ......................... 435/6, 91.2, 810; 536/23.1

(56) References Cited

U.S. PATENT DOCUMENTS

| | | | |
|---|---|---|---|
| 4,358,535 A | 11/1982 | Falkow et al. |
| 4,563,417 A | 1/1986 | Albarella et al. |
| 4,683,195 A | 7/1987 | Mullis et al. |
| 4,683,202 A | 7/1987 | Mullis |
| 4,942,124 A | 7/1990 | Church |
| 4,962,020 A | 10/1990 | Tabor et al. |
| 5,008,182 A | 4/1991 | Shinsky et al. |
| 5,124,247 A | 6/1992 | Ansorge |
| 5,171,534 A | 12/1992 | Smith et al. |
| 5,176,995 A | 1/1993 | Sninsky et al. |
| 5,219,727 A | 6/1993 | Wang et al. |
| 5,283,171 A | 2/1994 | Mamos et al. |
| 5,403,707 A | 4/1995 | Atwood et al. |
| 5,409,810 A | 4/1995 | Larder et al. |
| 5,427,911 A | 6/1995 | Ruano et al. |
| 5,451,512 A | 9/1995 | Apple et al. |
| 5,453,355 A | 9/1995 | Birkenmeyer et al. |
| 5,545,527 A | 8/1996 | Stevens et al. |

(List continued on next page.)

FOREIGN PATENT DOCUMENTS

| | | |
|---|---|---|
| EP | 403 333 | 10/1992 |
| WO | WO 9215711 | 9/1992 |
| WO | WO 92/16180 | 10/1992 |
| WO | WO 9219771 | 11/1992 |
| WO | WO 93/13223 | 7/1993 |
| WO | WO 9723650 | 7/1997 |
| WO | WO 9724974 | 7/1997 |

OTHER PUBLICATIONS

Chamberlain et al., "Detection of Gene Deletions Using Multiplex Polymerase Chain Reactions", *Meth. Molec. Biol.* 9: 299–312 (1991).

Ellison et al., "Detection of Mutations and Polymorphisms Using Fluorescence–Based Dideoxy Fingerprinting (F–ddf)", *Biotechniques* 17: 742–753 (1994).

Eisenstein, B.I., "The Polymerase Chain reaction", *New Engl. J. Med.* 322: 178–183 (1990).

Murakawa et al., "Direct Detection of HIV–1 RNA from AIDS and ARC Patient Samples", *DNA* 7: 287–295 (1988).

Ruano et al., "Coupled Amplification and Sequencing of Genomic DNA", *Proc. Nat'l Acad Sci* (USA) 88: 2815–2819 (1991).

Wiemann et al., "Simultaneous On–Line DNA Sequencing on Both Strands with Two Fluorescent Dyes", *Anal. Biochem* 224: 117–121 (1995).

Sarkar et al., "Dideoxy Fingerprinting (ddf) : A Rapod and Efficient Screen for the Prescence of Mutations" *Genomics* 13 441–443 (1992).

Lin et al., "Characterization of Genetic Defects of Hemophilia A in Patients of Chinese Origin" *Genomics* 18: 496–504 (1993).

*Primary Examiner*—Kenneth R. Horlick
(74) *Attorney, Agent, or Firm*—Holland & Hart LLP

(57) ABSTRACT

Quantitative and qualitative analysis of a nucleic acid analyte in a sample suspected to contain the nucleic acid analyte if achieved by first preparing a reaction mixture containing the sample and a known amount of an internal quantitation standard. At least a first aliquot of the reaction mixture is combined with a set of amplification reagents effective to amplify nucleic acids in the reaction mixture. The set of reagents includes at least one primer pair which is effective to amplify a first region of the nucleic acid analyte if present in the sample to produce a first amplified sample fragment and to amplify at least a portion of the internal quantitation standard to produce a control fragment. Amplification results in the formation of an amplification product mixture containing first amplified sample fragments and control fragments when the nucleic acid analyte is present in the sample, and only control fragments when the nucleic acid analyte is not present in the sample. The relative amounts of first amplified sample fragments and control fragments are analyzed to quantify the amount of nucleic acid analyte in the sample, and the sequence of the first amplified sample fragments is determined to assess the qualitative characteristics of any nucleic acid analyte. The internal quantification fragment is derived from the analyte nucleic acid by the incorporation of a plurality of sequence variations. These sequence variations include at least a first sequence variation effective to render the internal quantitation standard distinguishable from the first amplified sample fragment, and a second sequence variation effective to substantially eliminate the production of sequencing products from interaction of the internal quantitation standard and the first sequencing primer.

18 Claims, 7 Drawing Sheets

U.S. PATENT DOCUMENTS

| | | |
|---|---|---|
| 5,629,153 A | 5/1997 | Urdea |
| 5,795,722 A | 8/1998 | Lacroix et al. |
| 5,834,189 A | 11/1998 | Stevens et al. |
| 5,837,464 A | 11/1998 | Capon et al. |
| 5,856,088 A | 1/1999 | McDonough et al. |
| 5,888,736 A | 3/1999 | Lacroix et al. |
| 5,977,086 A | 11/1999 | Lisziewicz et al. |
| 6,017,699 A * | 1/2000 | Jordan ............... 435/6 |
| 6,087,093 A | 7/2000 | Lieven et al. |

* cited by examiner

METHOD AND KIT FOR QUANTITATION AND NUCLEIC ACID SEQUENCING OF NUCLEIC ACID ANALYTES IN A SAMPLE

This application is a continuation-in-part of U.S. patent application Ser. No. 09/818,182, filed Mar. 27, 2001, now U.S. Pat. No. 6,653,107, which is a continuation of U.S. patent application Ser. No. 09/418,720, filed Oct. 15, 1999, now U.S. Pat. No. 6,265,152, which is a continuation-in-part of U.S. patent application Ser. No. 08/938,641, Sep. 26, 1997, now U.S. Pat. No. 6,007,983 and a continuation-in-part of U.S. patent application Ser. No. 08/819,912 filed Mar. 18, 1997, now U.S. Pat. No. 5,795,722, all of which are incorporated herein by reference.

BACKGROUND OF THE INVENTION

This invention relates to a method and kit for quantifying and at least partially sequencing a nucleic acid analyte that is present in a sample. The nucleic acid analyte may be from an infectious organism that is present in a patient sample.

Academic and commercial interest in nucleic acid diagnostics has, to date, focused on qualitative assays. This type of assay determines the presence or absence in a patient sample of a specific gene mutation or infectious pathogen. Molecular assays which achieve these goals are well known. Many rely on amplification techniques, known to those skilled in the art such as the polymerase chain reaction (PCR), NASBA or 3SR, with or without hybridization probing. Others such as Digene Hybrid Capture Assays (DiGene Diagnostics Inc.) do not require amplification prior to detection and are generally less sensitive. Assays have been developed for many infectious pathogens such as *Chlamydia trachomatis*, Human Immunodeficiency Virus Type 1 (HIV-1) and Type 2 (HIV-2), and human papilloma virus (HPV). Some of these tests have been launched commercially by Roche Diagnostic Systems, Abbott Laboratories and others.

Quantitative assays of nucleic acid analytes also prove useful in diagnosis of a variety of medical disorders. For example, viral load in HIV infection may be correlated with increased risk of clinical progression of HIV disease (Mellors. J. W. et al. (1995). Quantitation of HIV-1 RNA in plasma predicts outcome after seroconversion. Ann. Intern. Med. 122: 573–579). While this example is best known, other quantitative applications also have clinical and commercial interest, such as quantitation of human papilloma virus in PAP smears. (Cuzick, J. et al. (1994) Type-specific human papillomavirus DNA in abnormal smears as a predictor of high-grade cervical intraepithelial neoplasia. Br. J. Cancer 69:167–171; Bavin P. J. et al. (1993) Use of semi-quantitative PCR for human papillomavirus DNA type 16 to identify women with high grade cervical disease in a population presenting with a mildly dyskaryotic smear report. Br. J. Cancer 67:602–605.)).

Notwithstanding their usefulness, quantitative assays of nucleic acid analytes have lagged behind in development. The delay may in part be attributed to technology barriers. Most instruments and methods provide inadequate dynamic range for measuring quantities, thus requiring labor intensive techniques such as multiple serial dilutions and repeat reactions. Further, until recently, PCR methods have been perceived as unreliable for quantitation due to the possibility of contamination and non-linear enzyme kinetics.

The AMPLICOR HIV-1 MONITOR (Roche Molecular Systems) test is a quantitative molecular assay for HIV RNA levels in blood. The assay is performed on HIV-1 and a subset of HIV-2 RNA found in 200 µL of blood plasma. The plasma sample is lysed and RNA is reverse transcribed then amplified by PCR. The reaction products are quantified by a probe based photometric assay and compared to the levels of a control RNA of known quantity that is added to the plasma sample. The control RNA is reverse transcribed along with the sample RNA and co-amplified using the same amplification primers. Six serial dilutions are necessary to detect across the full range of detectable viral load: 400 copies to 750,000 copies per ml. The test requires that for samples over 750,000 copies, (over 2.2 million copies per ml have been detected) the original patient sample must be diluted. The AMPLICOR assay therefore quantifies across the full range of possible values by a series of multiple dilutions. The AMPLICOR assay does not determine which sub-type or sub-types of HIV-1 are present, and it does not establish if HIV-2 was amplified.

Other quantitative HIV assays have been reported. Some of these papers, incorporated herein by reference, include:

Mulder, J et al. Rapid and simple PCR assay for quantitation of human immunodeficiency virus type 1 RNA in plasma: Application to acute retroviral infection. J. Clin. Micro. 32:292–300

Dewar, R. L. et al, 1994 Application of branched DNA signal amplification to monitor human immunodeficiency virus type 1 burden in human plasma. J. Infect. Dis. 170:1172–1179 van Gemen, B. et al. 1993 Quantification of HIV-1-1 RNA in plasma using NASBA during HIV-1-1 primary infection. J. Vir. Meth. 43:177–188.

The possibility of integrating a quantitative nucleic acid assay with a qualitative assay, such as sequencing of the nucleic acid, has not been achieved or proposed by previous workers. The advantage of an integrated test would be enormous, however, particularly in the case of evaluation of HIV infections. For example, not only could pathogen load be determined but also the exact serovar (or variety) of the pathogen could be determined. This would allow doctors and patients to know if treatments were effecting not only the quantity but also the variety of pathogen. In addition, a simplified assay would provide substantial economies of scale.

It is an object of the present invention to provide a method and kit for quantifying and determining the nucleic acid sequence of a nucleic acid analyte that is present in a patient sample.

It is a further object of the present invention to provide a method and kit for the quantifying and genotyping of HIV virus present in a patient sample.

SUMMARY OF THE INVENTION

These and other objects of the invention are achieved by a method for quantitative and qualitative analysis of a nucleic acid analyte in a sample suspected to contain the nucleic acid analyte, comprising the steps of:

(a) preparing a reaction mixture containing the sample and a known amount of an internal quantitation standard;

(b) combining at least a first aliquot of the reaction mixture with a set of amplification reagents effective to amplify nucleic acids in the reaction mixture, said reagents including at least one primer pair which is effective to amplify a first region of the nucleic acid analyte if present in the sample to produce a first amplified sample fragment and to amplify at least a portion of the internal quantitation standard to produce a control fragment;

(c) amplifying nucleic acid analyte from the sample and the internal quantitation standard in the reaction mixture using the first pair amplification product mixture containing first amplified sample fragments and control fragments when the nucleic acid analyte is present in the sample, and only control fragments when the nucleic acid analyte is not present in the sample;

(d) analyzing the relative amounts of first amplified sample fragments and control fragments in the amplification product mixture to quantify the amount of nucleic acid analyte in the sample; and (e) determining the sequence of the first amplified sample fragments in the amplification mixture to determine the qualitative characteristics of any nucleic acid analyte in the sample using at least a first sequencing primer.

In accordance with an embodiment of the method of the invention, the internal quantification fragment is derived from the analyte nucleic acid by the incorporation of a plurality of sequence variations. These sequence variations include at least a first sequence variation effective to render the internal quantitation standard distinguishable from the first amplified sample fragment, and a second sequence variation effective to substantially eliminate the production of sequencing products from interaction of the internal quantitation standard and the first sequencing primer.

For evaluation of HIV and other genes which contain multiple regions of potential genetic variations and interest, this method is preferably utilized as part of a broader method in which the genome is evaluated in several parts. For example, in the case of HIV-1, the genome may be evaluated in one part for evaluation of the protease gene and three parts for evaluation of the beginning, middle and end portions of the reverse transcriptase gene. In accordance with this embodiment of the invention, separate aliquots of the reaction mixture containing the internal quantification standard are preferably utilized for each of the regions of interest and are amplified using distinctive pairs of amplification primers suitable for amplification of each of the regions. The internal quantification standard preferably includes sequence variations such that it is amplified by only one of the pairs of amplification primers.

DETAILED DESCRIPTION OF THE INVENTION

Figure 1:
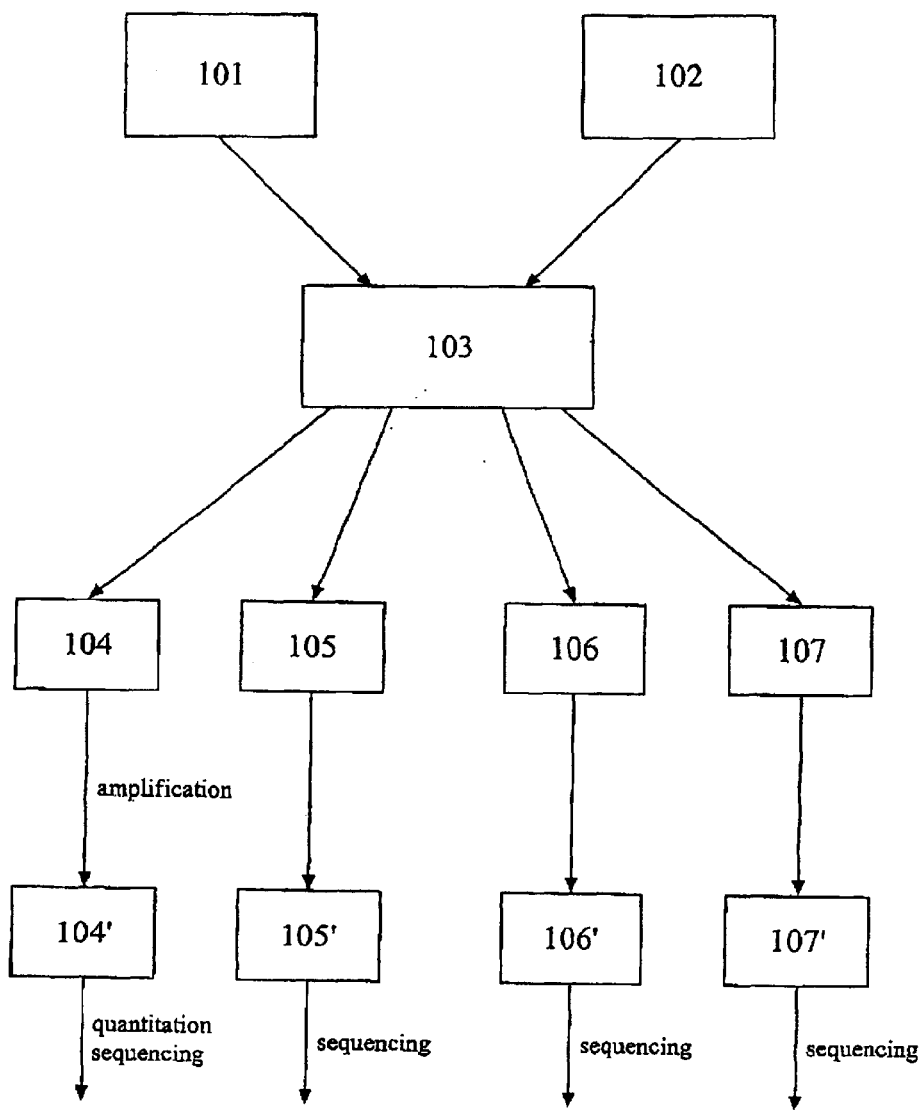
FIG. 1 provides a schematic summary of an embodiment of the method of the invention.

While this application generally uses terms relating to the method of the invention in their normal manner, the following definitions are provided to avoid ambiguity:

"Amplification" means the process of increasing the relative abundance of one or more specific genes or gene fragments in a reaction mixture with respect to other genes. A method of amplification which is well known by those skilled in the art is the polymerase chain reaction (PCR) as described in U.S. Pat. Nos. 4,683,194, 4,683,195 and 4,683,202, which are incorporated herein by reference. The method is also explained in texts such as Current Protocols in Molecular Biology, (Eds. Ausubel, F. M. et al., (John Wiley & Sons; 1995)). The PCR process involves the use of pairs of primers, one for each complementary strand of the duplex DNA (wherein the coding strand is referred to as the "sense strand" and its complementary strand is referred to as the "anti-sense strand"), that will hybridize at sites located on either side of a region of interest in a gene. Chain extension polymerization is then carried out in repetitive cycles to increase the number of copies of the region of interest exponentially. The amplified polynucleotide may be used as the template for a sequencing reaction. Gelfand et al. have described a thermostable enzyme, "Taq polymerase", derived from the organism *Thermus aquaticus*, which is useful in this amplification process (see U.S. Pat. Nos. 4,889,818; 5,352,600; and 5,079,352 which are incorporated herein by reference). Alternative amplification techniques such as NASBA, 3SR, Qb Replicase, and Branched Chain Amplification are known and available to persons skilled in the art. The term "RT-PCR" refers generally to amplification which includes a reverse transcription step to permit amplification of RNA sequences.

"Patient sample" means a sample collected from a patient which may contain a nucleic acid analyte such as an infectious pathogen. Patient samples include but are not limited to blood samples, tissue samples, biopsy samples, excretions and secretions such as urine, feces or oral or genital mucosal swabs.

"Primer" means a polynucleotide generally having a length of 5–50 nucleotides which can serve to initiate a chain extension reaction. A "primer pair" is a pair of primers which specifically hybridize to sense (coding) and antisense (non-coding) strands of a duplex polynucleotide to permit amplification of the region lying between the primers of the pair. Sequencing can be performed using a single primer or a primer pair.

"Reverse transcription" is the process of generating a DNA complement to an RNA molecule, and is generally accomplished with the use of a reverse transcriptase enzyme. A primer may be used to initiate polymerization; this primer may be one of a primer pair later used for PCR amplification. The RNA molecule is then separated from the copied DNA ("cDNA") or degraded by an RNAse H activity of an enzyme thus allowing the second strand of cDNA to be generated by a template dependent DNA polymerase. This method is disclosed in Units 3.7 and 15.4 of Current Protocols in Molecular Biology, Eds. Ausubel, F. M. et al, (John Wiley & Sons; 1995) which are incorporated herein by reference.

"Sequence variation" refers to differences in sequence between the expected sequence of the analyte nucleic acid and the internal quantitation standard. These sequence variations may take the form of deletions, insertions, or point substitutions relative to the expected sequence of the analyte nucleic acid, as reflected in the primers selected for amplification and sequencing.

"Sequencing" or "DNA Sequencing" means the determination of the order of nucleotides in at least a part of a gene. A well known method of sequencing is the "chain termination" method first described by Sanger et al., PNAS (USA) 74(12): 5463–5467 (1977) and detailed in SEQUENASE™ 2.0 product literature (Amersham Life Sciences, Cleveland) and more recently elaborated in European Patent EP-B1-655506 all incorporated herein by reference. Basically, in this process, DNA to be sequenced is isolated, rendered single stranded, and placed into four vessels. In each vessel are the necessary components to replicate the DNA strand, which include a template-dependent DNA polymerase, a short primer molecule complementary to the initiation site of sequencing of the DNA to be sequenced and deoxyribonucleotide triphosphates for each of the bases A, C, G and T, in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate ("ddA"), dideoxyguanosine triphosphate ("ddG"), dideoxycytosine triphosphate ("ddC"), dideoxythymidine triphosphate ("ddT"). In each vessel, each piece of the isolated DNA is hybridized with a primer. The primers are then extended, one base at a time to form a new nucleic acid polymer complementary to the template DNA. When a dideoxynucleotide is incorporated into the extending polymer, the polymer is prevented from further extension. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

"Single Track Sequencing" means the method disclosed in U.S. Pat. No. 5,834,189, assigned to the assignee of the instant invention and incorporated herein by reference. In Single Track Sequencing the positions of less than all four, and preferably of only one nucleotide of a target sequence are determined. Single Track Sequencing provides a fingerprint or bar-code of the target sequence that may be sufficient to distinguish it from all other known varieties of the sequence. Throughput is increased by reducing the number of reactions and electrophoresis runs required to identify a sequence.

"Specific hybridization" means hybridization of an oligonucleotide to its exact complement, or a complement that is sufficiently similar that hybridization may occur in conditions that are of intermediate stringency.

"Target sequence" means the nucleic acid sequence that is the target of investigation. In PCR amplifications, the target sequence is bounded by and includes the sites of specific hybridization of the primer pair.

The present invention relates to a method and kit for quantifying and at least partially determining the nucleic acid sequence of a nucleic acid analyte that is present in a patient sample. This integrated test simplifies a series of laboratory tasks and provides physicians with better information about a patient's condition than previously described tests.

The general format of one embodiment of the method of the invention is illustrated in FIG. 1. Total nucleic acids (DNA or RNA) 101 are prepared from a known amount of patient sample. The preparation 101 is mixed with an internal quantitation standard 102 of known quantity to create a reaction mixture 103. This reaction mixture is divided into a plurality of aliquots 104, 105, 106 and 107, or as many aliquots as are needed to provide one aliquot for each region to be evaluated. Each of these aliquots is amplified using a primer pair which is effective to amplify the region of interest for that reaction, and the reaction products (104', 105', 106' and 107') are then sequenced. In addition, one of the primer pairs is designed to also amplify the internal quantitation standard (IQS). Comparison of the amounts of amplified IQS and the amount of amplified analyte nucleic acid in the amplification product (for example 104') is used to quantify the amount of analyte nucleic acid present.

Figure 2A:
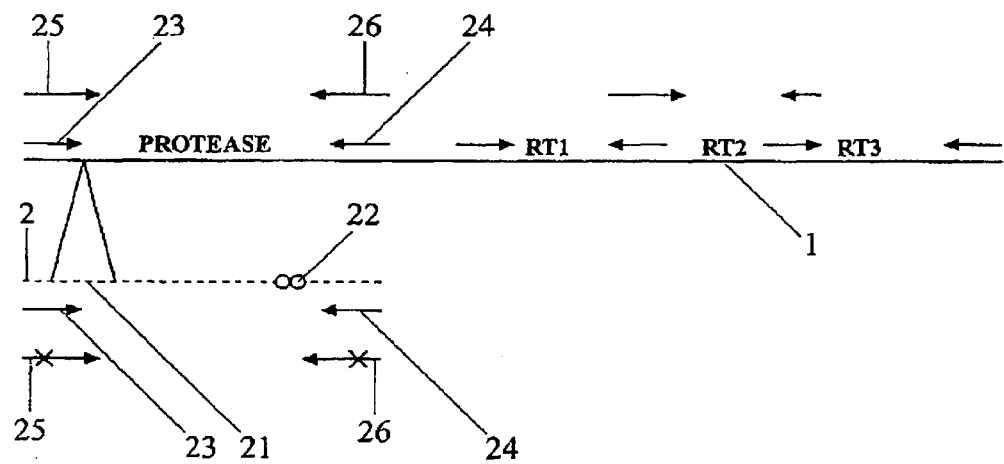
FIGS. 2A and 2B show two exemplary embodiments of the relationship of the internal quantification standard and primers for analysis of the HIV-1 gene.

An important aspect of the invention is the selection of the IQS and the amplification and sequencing primers so that they work in concert to provide for effective analysis of the nucleic acid analyte in the sample. To exemplify and elucidate this selection process, FIGS. 2A and B show the relationship of the IQS and primers for analysis of the HIV-1 gene, assuming analysis of the HIV-1 genome in four portions: a first portion for the protease gene, and three portions for the beginning (RT1), middle (RT2) and end (RT3) of the reverse transcriptase gene. In FIG. 2A, the HIV-1 RNA from the patient sample is indicated by a solid line 1, while the IQS is indicated by a dashed line 2. The IQS 1 is derived from the HIV-1 sequence of the protease gene by the introduction of a plurality of sequence variations, for example insertion 21 and point mutations 22. These sequence variations are positioned in a defined relationship relative to the primers to be employed for amplification and sequencing. Thus, amplification primers 23, 24 are effective to amplify both the sample HIV gene 1 and the IQS 2, while sequencing primers 25, 26 are effective for generation of sequencing fragments from the sample HIV gene 1, but not from the IQS 2.

Figure 2B:
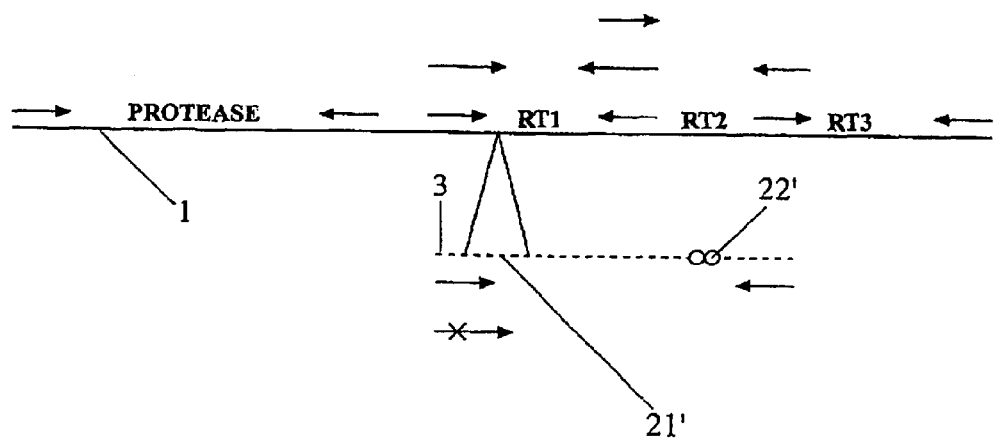

FIG. 2B shows another embodiment of an IQS in accordance with the invention. In this case, the IQS 3 is derived from the HIV-1 sequence of the reverse transcriptase gene by the introduction of a plurality of sequence variations, for example insertion 21' and point mutations 22'. These sequence variations are positioned in a defined relationship relative to the primers to be employed for amplification and sequencing in the same manner as those shown in FIG. 2A.

Figure 3A:
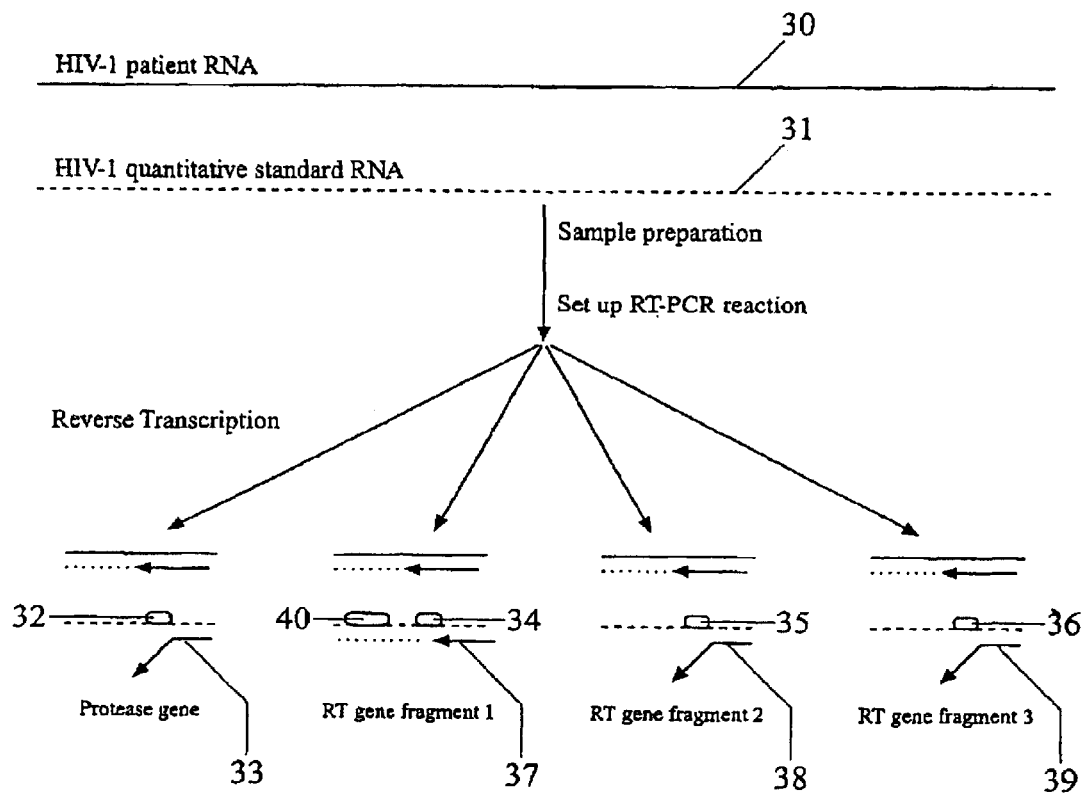
FIGS. 3A–D show a schematic outline of the qualitative and quantitative steps of an embodiment of the method of the invention.
Figure 3B:
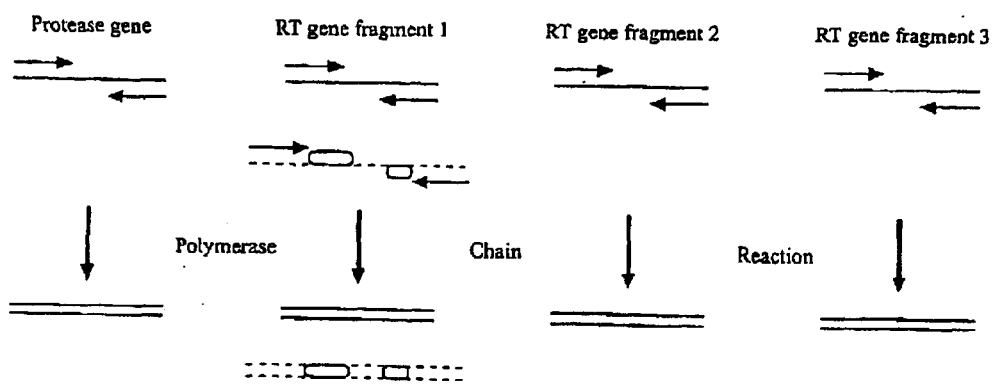
Figure 3C:
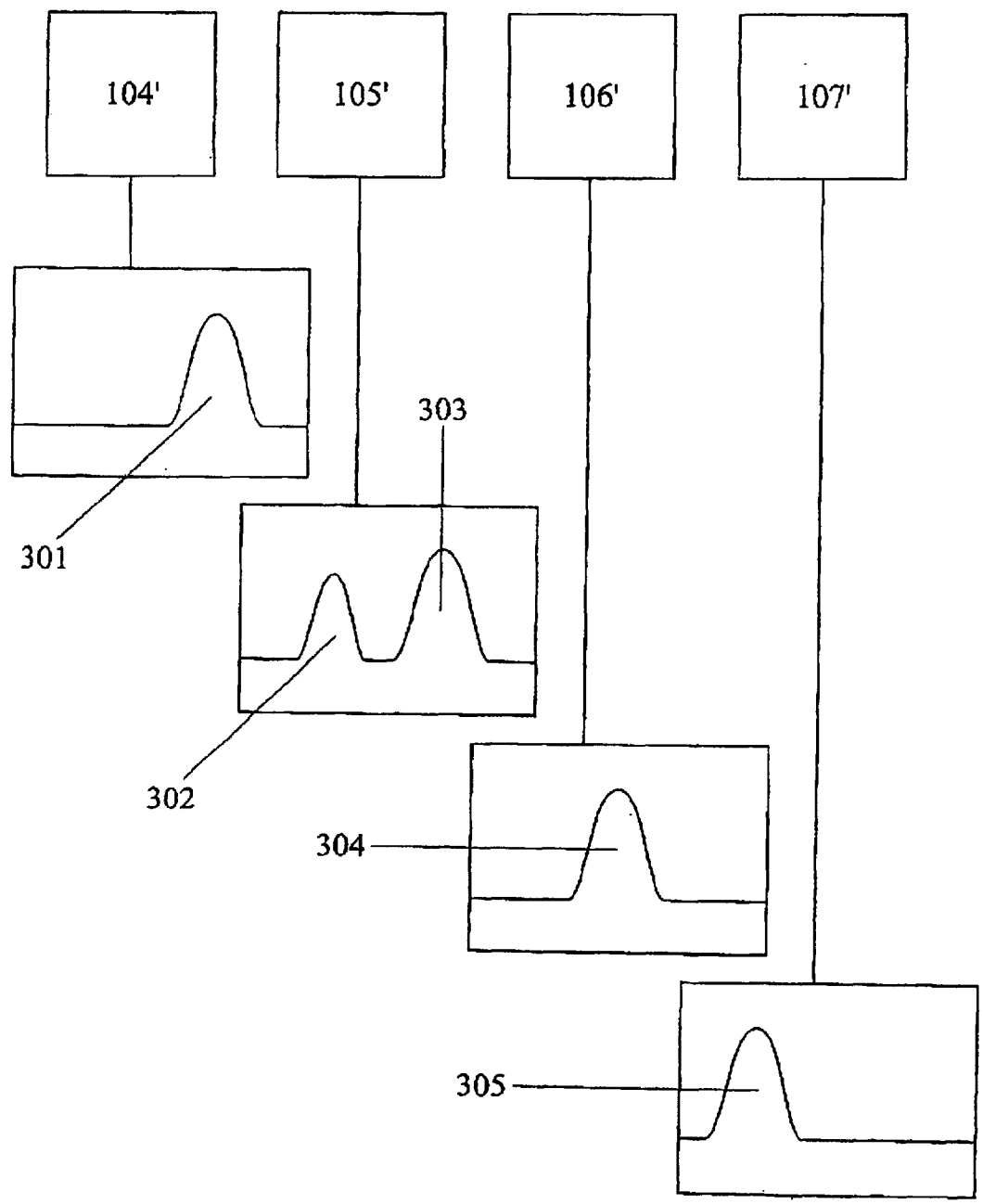

FIGS. 3A–C show a schematic outline of the qualitative and quantitative steps of an embodiment of the method of the invention. The HIV-1 patient RNA 30 and the IQS 31 are combined in a sample and processed by RT-PCR in four batches. The IQS 31 utilized in the embodiment shown in FIGS. 3A–C overlaps with the protease and reverse transcriptase genes of the HIV-1 patient RNA 30. Five sequence variations are introduced into the IQS as shown in FIG. 3A. Variation 32 overlaps with the site of a reverse transcription primer 33 used for amplification of the protease gene in such a way that reverse transcription of the IQS in the protease region is disrupted. Variations 35 and 36 overlap with the sites of reverse transcription primers 38, 39 used for reverse transcription of portions of the reverse transcriptase gene in such a way that reverse transcription of the IQS in the RT regions 1RT2 and RT3 is disrupted. Variation 40 is in insertion which changes the size of the IQS fragment produced during amplification of the RT1 region. Variation 34 is a variation which will disrupt the sequencing of the RT1 IQS fragment, but which does not interfere with reverse transcription using reverse transcription primer 37 or subsequent amplification.

FIG. 3B shows the next phase of the reaction. The reverse transcription products from the four reverse transcription reactions are each amplified using a PCR procedure. In the case of the first, third and fourth reactions, there is only one reverse transcription product, and thus only one amplification process produced. In the case of the first RT gene fragment, reverse transcription produces a product from both the sample and the IQS, so two products are amplified. FIG. 3C shows the results of this amplification schematically. In the first amplification reaction (104'), only the protease gene is amplified to produce amplified product 301. In the second amplification reaction (105'), both the beginning portion of the RT gene and the IQS are amplified to produce two reaction products, 302 and 303. In the third (106') and fourth (107') amplification reactions, only the middle and end portions of the RT gene are amplified to produce amplification products 304 and 305, respectively.

At this stage of the process, two analytical procedures are used. As a first procedure, the relative amounts of products 302 and 303 are evaluated as a measure of the amount of the nucleic acid analyte in the sample. As a second procedure, which may be performed contemporaneously with, before or after the quantitative evaluation, the positions of at least one species of nucleotide base within products 301, 302, 304 and 305 are determined. Complete sequence analysis of the positions of all four bases may also be performed, as well as analysis of any intermediate number of bases.

As noted above, the IQS includes a sequence variation which is designed to make amplification product 303 distinguishable from amplification product 302. In one embodiment of the invention, this sequence variation is an insertion or deletion mutation which results in a difference in length between the two products. When a sequence variation of this type is used, the relative quantities of amplification products 302 and 303 can be determined by separating an aliquot of the amplification product mixture and detecting the peaks. The ratio of the peak size resulting from the amplification of the sample to the peak size resulting from amplification of the IQS can be used to calculate the amount of the analyte in the sample because a known amount of IQS was introduced into the starting reaction mixture.

Quantitation is performed by loading part of the reaction mixture on an automated fluorescence detection electrophoresis instrument that has a dynamic range broad enough to include the quantitative range of measurements desired. Such an instrument is disclosed in U.S. Pat. No. 5,710,628 and PCT Patent Publication No. WO 96/18892, which are incorporated herein by reference and embodied in the MicroGene Blaster Automated DNA Sequencer (Visible Genetics Inc., Toronto). An improved version of this instrument is disclosed in U.S. patent application Ser. No. 08/819,910, filed Mar. 18, 1997 which is incorporated herein by reference. The peaks corresponding to the amplified analyte fragment and amplified IQS control fragment are quantified by measuring the area under each peak of the output signal. Because the IQS is added in known amount, the amount of nucleic acid in the original patient sample can be calculated by extrapolation.

While the use of insertions or deletions as the sequence variation which permits one to distinguish the amplifications products 302 and 303 is a preferred approach because of the convenience of the detection system, other forms of sequence variation may also be employed. For example, one can introduce a distinctive site for hybridization of a labeled probe into the IQS. By utilizing distinctively labeled probes which bind to this site in either the analyte or IQS form and measuring the relative amounts of each probe that is bybridized to an amplification product, one can quantify the amount of analyte in the sample. Other forms of detectable mutations might also be used, including without limitation mutations which create or eliminate a cleavage site for a restriction endonuclease.

Figure 3D:
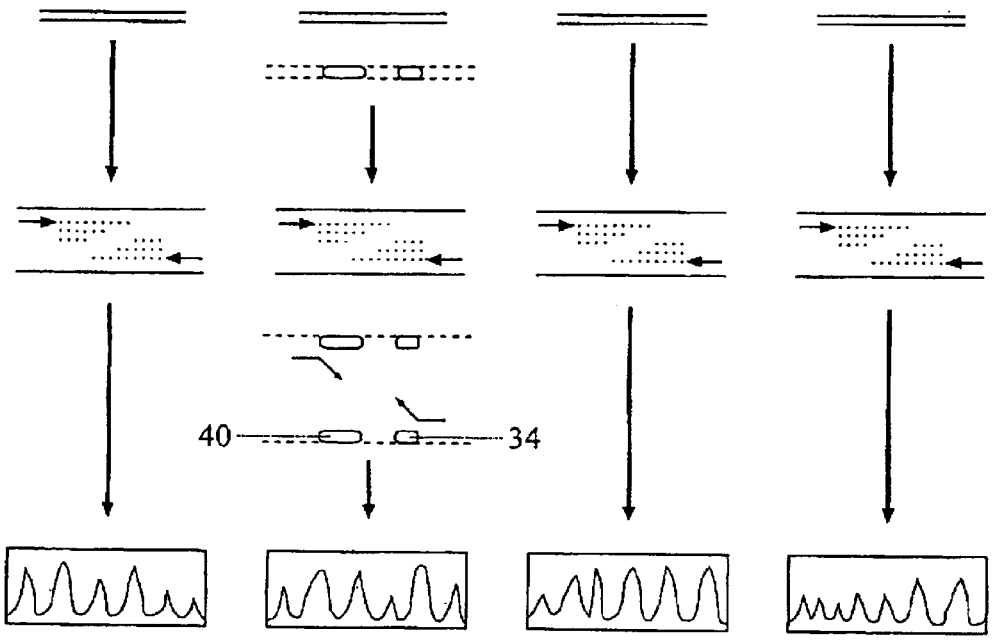
Figure 4:
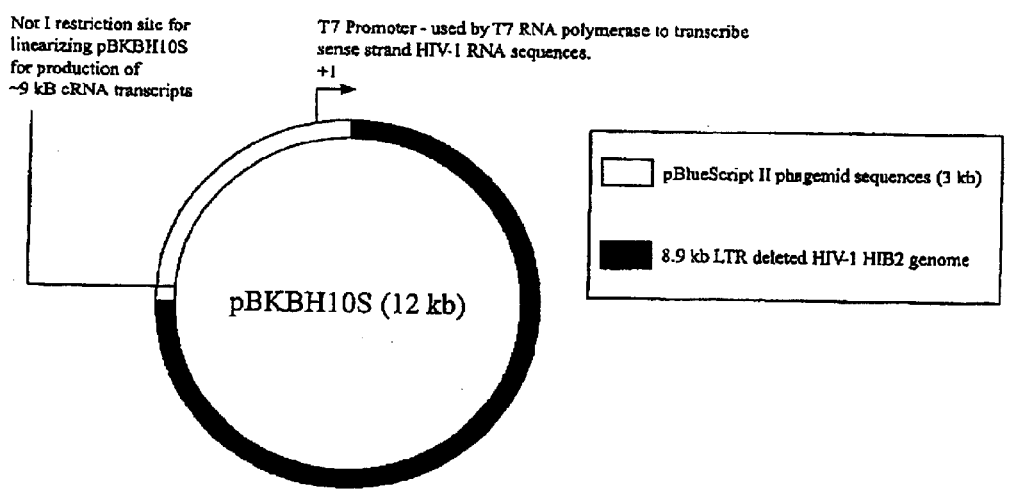
FIG. 4 shows a map of the pBKBH10S.

The second analysis procedure is the sequencing of the amplified portions of the sample nucleic acid. This sequencing procedure is shown schematically in FIG. 3D. The first, third and fourth reaction mixtures include only one species of amplified product which is sequenced. The second reaction mixture includes both the sample and the IQS amplified products. However, the IQS includes sequence variations 34 and 40 which are effective to substantially eliminate the production of sequencing products as a result of interaction (hybridization plus chain extension) between the IQS and the sequencing primer used for qualitative evaluation of the first amplified analyte fragment. While ideally no sequencing products are produced from the IQS, it is sufficient if the quantity of such sequencing fragments produced is small in comparison to the quantity of sequencing fragments generated from the analyte, such that the analysis of the analyte sequence is not compromised. This threshold is what is meant by the term "substantially eliminated."

The sequencing steps used to evaluate the first and any additional amplified analyte fragments can be performed using any known sequencing methodology. Preferably, sequencing is performed using a form of sequencing based on the Sanger chain extension technique. This can make use of capture moieties, such as biotin, introduced as part of the amplification primers to permit separation of the amplified fragments from other reaction components, but this is not required. If such separation is utilized, solid support such as avidin coated-magnetic beads can be used to to capture the biotin-labeled fragments. With or without such separation, the amplified products are combined with reagents suitable for DNA or RNA sequencing. Sequencing methods such as Cycle Sequencing as disclosed in European Patent No. 655,506, which is incorporated herein by reference, or CLIP™ Sequencing using the thermally-stable polymerase THERMOSEQ-UENASE™ or similar enzymes as disclosed in U.S. Pat. Nos. 5,789,168 and 5,830,657, both of which are incorporated herein by reference, are preferred. In addition, the method may employ Single Track Sequencing to provide a finger-print or bar-code identity of the target sequence. Once the identity of pathogen variety, or mixture of varieties, is determined, it is reported to the patient file along with the quantitative data previously determined.

When sequencing procedures are utilized which make use of two sequences primers, it is preferred that sequence variations be included in the IQS which impair hybridization with each of these primers. This can be accomplished as shown in FIGS. 2A and B, where the insertion mutation has the duel function of making the IQS-amplification product distinguishable in size from the sample amplification product and of disrupting the hybridization with the sequencing primer. Alternatively, a third sequence variation can be utilized.

Because the fragments used in sequencing are amplified in the original amplification reaction, a separate amplification need not be performed, saving time and effort to reach the desired result. Further, sequencing can serve as an additional control for the quantitative assay. Results can be reported rapidly and accurately.

Within the basic technique described above, there are numerous variations possible. For example, method shown above describes the addition of the IQS to form a common reaction mixture used for each of the amplification reactions, even though the IQS is only amplified in one of the reaction mixtures. The incorporation of the IQS at the initial stage is preferred, since it acts as an internal control for possible degradation of the nucleic acid molecules (DNA or RNA) during processing, but it is not mandatory to the success of the method of the invention. Thus, the sample could be divided into aliquots prior to the addition of the IQS, with the IQS being added to only the aliquot in which it will be amplified. In this case, the additional sequence variations included to avoid amplification of the IQS in the second and subsequent amplification reactions would not be required. Similarly, the IQS may be designed in such a way that it is amplified in more than one of the amplification reactions to provide redundancy in the quantification procedure. In general, however, the methodology outlined in FIGS. 1–4 is preferred.

The method of the invention can be applied to samples containing either a DNA or an RNA nucleic acid analyte. Thus, the method is conveniently applied to diagnosis of infectious pathogens such as HIV-1 and -2, HPV or *C. trachomatis*. The method of the invention can be applied to HIV-1, and other RNA viruses by direct application to viral RNA, or it can be performed on corresponding cDNA or proviral DNA which has been integrated in the genome of a host cell. It will be appreciated that the IQS employed is preferably one which closely matches the analyte of interest, since this allows the IQS to function as an internal control for the chemistry as well as a quantitation standard. The IQS is therefore preferably of the same chemical nature as the analyte (RNA IQS for RNA analyte, DNA IQS for DNA analyte) and is of an overall size and configuration which is substantially similar to the analyte apart from the necessary sequence variations. Such IQS molecules can be derived from the analyte with which they are to be used using genetic engineering techniques.

Figure 5:
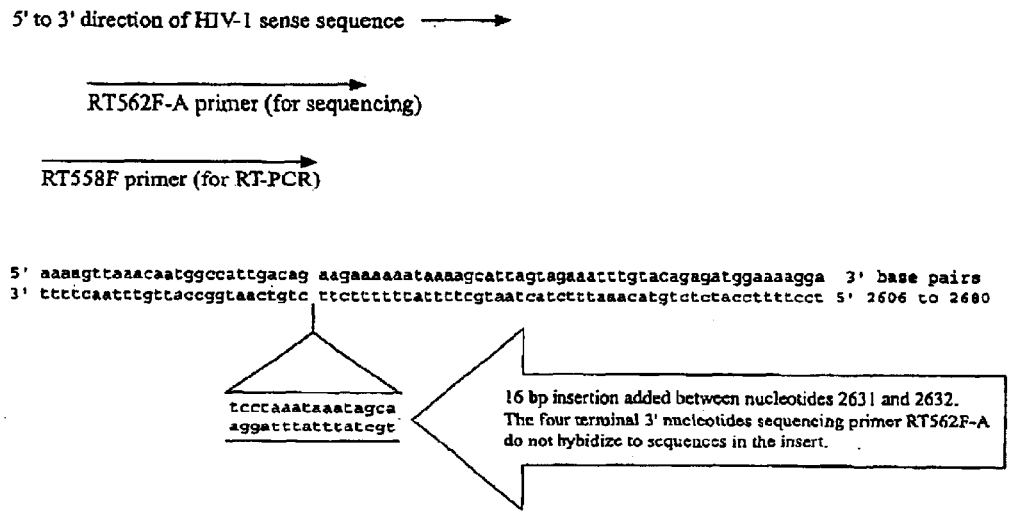
FIG. 5 illustrates the introduction of sequence variations into the plasmid pBKBH10S to create a plasmid useful as an IQS when analyzing for HIV-1.
Figure 6:
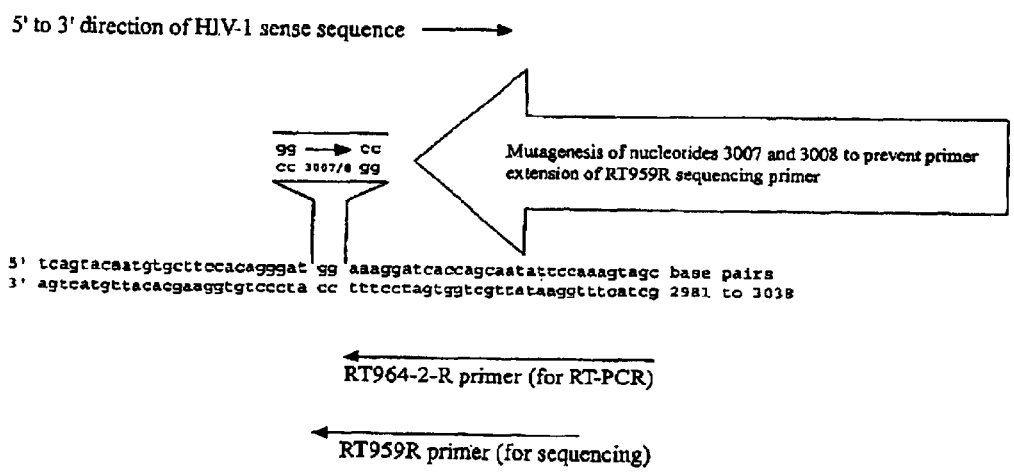
FIG. 6 illustrates the introduction of sequence variations into the plasmid pBKBH10S to create a plasmid useful as an IQS when analyzing for HIV-1.

By way of example, and without the intent to limit the scope of protection, a synthetic nucleic acid segment for use as the IQS in the evaluation of HIV-1 analytes was constructed by performing PCR-based site directed mutagenesis of a sequence derived from the reverse transcriptase (RT) gene of HIV-1 wild-type strain HXB2 [Seq. ID No. 1]. The procedure used for producing the construct was similar to methods described by Silver et al. for PCR based site-directed mutagenesis (Silver et al. 1995, PCR Strategies). Mutagenic PCR primers, RT558-INS-F [Seq. ID No.2] and RT964-MUT-R [Seq. ID No.3], were designed and synthesized for amplification of HIV-1 RT gene sequences from the plasmid pBKBH10S (FIG. 4) and incorporation of the necessary modifications required for the IQS sequence (FIGS. 5 and 6). pBKBH10S is a plasmid containing an 8.9 kb LTR deleted segment of the HIV-1 HXB2 genome subloned into a pBluescript vector (Stratagene systems). pBKBH10S is described in Cheng et al., 1990 *Biotechnol* 2:23–31.

The orientation of the QS sequence in the resulting plasmid, pQSRTB, was such that transcription utilizing the plasmid's T7 promotor would produce sense strand HIV-1 sequence. For use as an IQS in the method of the invention, 5 μg of pQSRTB was linearized by digestion with Not I restriction enzyme (Boehringer Mannheim). The linearized plasmid was treated for RNase contamination by incubation with Proteinase K and purified by extraction prior to use as an IQS in the method of the invention.

At least one member of the primer pairs employed in the method of the present invention for amplification of the IQS and the corresponding region of the analyte is preferably labeled with a detectable label. Suitable labels include fluorescent labels such as fluorescein and cyanine dyes. A variety of such labels are known in the art. Fluorescent labels may also be included in other amplification primers for monitoring purposes, but this is not required.

Furthermore, as noted above, one of the primers of each pair used to amplify the analyte to produce amplified analyte fragments may be conjugated at its 5'-end to biotin or a similar moiety which will permit selective capture of primer. A biotin label allows the fragment to be purified from the original amplification mixture using avidin coated magnetic beads such as DYNABEADS—280 (Dynal, Oslo, Norway). Purification can improve the results of sequencing reactions but it is not generally necessary, depending on the design of the protocol.

The primer pairs selected for amplification of the analyte regions and the IQS are combined with aliquots of sample containing the nucleic acid analyte in a form accessible for amplification. In the case, of an RNA analyte, amplification of the sample must be proceeded by reverse transcription to create a DNA sequencing template. This step is conveniently achieved by the addition of the thermostable DNA polymerase isolated from *Thermus thermophilus*. This enzyme has reverse transcriptase activity in the presence of $Mn^{2+}$ and DNA polymerase activity under thermal processing conditions. (Myers, T. W. and D. H. Gelfand. 1991. Reverse transcription and DNA amplification by a *Thermus thermophilus* DNA polymerase. Biochemistry 30:7661–7666). Amplification primers are added to the reaction mixture, with chain extension reagents. In the first reduced temperature step, one primer hybridizes to the RNA and the primer is extended to generate one strand of cDNA. In the second step of high temperature thermal processing, the cDNA is copied by the reverse primer, thus generating a double stranded molecule, and leading to an exponential increase in cDNA amounts after repeated cycles.

The amplification reaction mixture is processed through a plurality of thermal cycles, generally 10 to 40 cycles, to produce an amplified product mixture containing conserved, control and sequencing fragments. The amplified product mixture in which amplification of the IQS is expected to occur is then loaded onto an electrophoresis gel and evaluated for the presence of detectable products from the amplification Some of the benefits of the present invention, notably the simplification that results from the use of the first amplified analyte fragment for both quantification and sequencing can be achieved regardless of the nature of the instrument on which the evaluation is performed. Thus, on an instrument with low or modest dynamic range, serial dilutions of the amplified product mixture can be loaded onto the electrophoresis gel for evaluation. Preferably, however, the analysis is performed on an instrument having a dynamic range that permits the detection of conserved and control fragments at concentrations spanning several (i.e. 3 or more) orders of magnitude.

The specific configuration of the instrument employed to measure the amount of conserved fragment and control fragment(s) on an electrophoresis gel will depend on the nature of the detectable labels employed, and persons skilled in the art will have no difficulty matching any given type of label with a compatible instrument. The preferred type of label affixed to the conserved and control fragments is a fluorescent label. Thus, instruments which are suitable for detection of fluorescent conserved and control fragments are discussed herein in detail.

As noted above, a substantial challenge in quantifying the amount of nucleic acid analyte in a sample is the broad range of concentrations which may be encountered, and the substantial differences which may exist between the concentration of the nucleic acid analyte and the concentration of the control nucleic acid. Since fluorescence intensity is generally (absent issues such as quenching, saturation of the fluorescent reagent or photochemical reaction) directly proportional to the amount of fluorescent compound present and the number of input photons of appropriate energy for excitation in the excitation beam, a simple linear calibration curve over a several serial dilutions of the sample can be used to determine the amount of nucleic acid in the original sample even in an instrument which lacks the dynamic range to accommodate substantial concentration differences between sample and control.

Preferably, however, the measurements are made with an instrument such as a MICROGENE BLASTER electrophoresis and DNA sequencing apparatus (Visible Genetics Inc., Toronto, Canada). The MICROGENE BLASTER has a dynamic range extending over about three orders of magnitude, since the instrument can detect a band when from about 1 attomol ($10^{-18}$) to about 1 femtomol ($10^{-15}$) of a single species of DNA loaded per well. Thus, the instrument makes it possible to eliminate serial dilutions from the laboratory protocol, and perform a single reaction, with a single control nucleic acid or set of control nucleic acids for each patient sample.

The structure of the current MICROGENE BLASTER apparatus is described in U.S. Pat. No. 5,710,628 and PCT Patent Publication No. WO 96/18892. Thus, a suitable apparatus is an apparatus for electrophoretic separation and detection of a plurality of samples, each labeled with a fluorophore and loaded into a lane of an electrophoresis gel, comprising:

(a) a housing adapted to receive an electrophoresis gel holder containing an electrophoresis gel loaded with the samples;

(b) a laser diode excitation source for providing an incident beam of coherent radiation of a frequency suitable for excitation of the fluorophore;

(c) a spot array generation grating for dividing the incident beam of coherent radiation into a plurality of excitation beamlets of the frequency suitable for excitation of the fluorophore and directing each excitation beamlet to an excitation/detection site on a different lane of the electrophoresis gel; and (d) an array of detectors aligned with the excitation/detection sites for collecting fluorescent emissions. The collected emissions are preferably processed using a computer program such as GENEOBJECTS™ signal processing and evaluation software (Visible Genetics Inc.), although the fundamental simplicity of the peak pattern detected (i.e., as few as two peaks in the case of a conserved fragment and a single control fragment) makes the use of very sophisticated peak identification algorithms generally unnecessary.

Although the MICROGENE BLASTER apparatus provides high dynamic range and is fully suitable for use in the invention, certain improvements can further increase the dynamic range of the instrument. Thus, a preferred high-dynamic range instrument for use in practicing the method of the invention is of the type described in U.S. patent application Ser. No. 08/819,910. This instrument incorporates one or more of the following approaches for increasing the dynamic range of the instrument:

(1) modulation of signal integration periods can be employed so that large signals are totaled at short time intervals and smaller signals are totaled at longer time intervals. This approach is disclosed in U.S. Pat. No. 5,786,142 which is incorporated herein by reference.

(2) the instrument can incorporate a beam splitter which produces a high intensity beam and a low intensity beam from each excitation/detection site and detects the two beams separately. When the signal strength is high, the low intensity beam will generally be below the saturation threshold of the detector, while when the signal strength is low, the high intensity beam is generally above the detection threshold of the detector.

(3) modulation of the intensity of the excitation beam can be used improve the dynamic range of the instrument. Thus, for example, is a 20 mW laser diode (which has a variable output of 1–20 mW) is used at power levels varying in a stepwise fashion from 1 mW at the low end to 20 mW at the high end, measurements can be taken during either the low power window and the high power window, depending on the strength of the signal.

If a peak is detected in the quantitation stage indicating the presence of the nucleic acid analyte in the sample, the next step in the method is the determination of the sequence of the sequencing fragment. Sequencing reactions may be performed by any means known in the art. A preferred method is to perform cycle sequencing using a labeled primer that specifically hybridizes to the sequencing fragment only, in the presence of chain extension reagents, one chain terminating reagent (such as ddTTP) and THERMOSEQUENASE (TM) enzyme (Amersham Life Sciences, Cleveland). The sequencing primer may be the same as one of the amplification primers, or it may be "nested", i.e. specifically hybridizing to a site not at the end of the fragment. The fluorescent label preferred for use on the Visible Genetics MicroGene Blaster is Cy5.5. If different instruments are used, different labels may be employed.

An alternative method for sequencing is to employ the CLIP™ sequencing technique, disclosed in U.S. Pat. Nos. 5,789,168 and 5,830,657 assigned to the assignee of the present application and incorporated herein by reference. In this method two primers similar to amplification primers are employed in a chain termination sequencing reaction. This generates chain terminated fragments from both strands of the template. Each primer is given a different detectable label so that when the results are run on an automated fluorescence sequencer with multi-dye detectors, both strands can be sequenced with a minimum number of steps.

The method of the present invention is conveniently practices with reagents provided in kit format, and such kits form an aspect of the present invention. Such a kit comprises, in packaged combination, (a) a first pair of amplification primers effective to amplify a first region of the nucleic acid analyte to produce a first amplification product;

(b) a first sequencing primer for generating sequencing fragments from the first amplification product; and (c) an internal quantitation standard. The internal quantitation standard comprises a nucleic acid polymer derived from the analyte nucleic acid by the incorporation of a plurality of sequence variations, including at least a first sequence variation effective to render a control fragment produced by amplification of the internal quantitation standard with the first pair of primers distinguishable from a first amplified sample fragment produced by amplification of the analyte nucleic acid with the first pair of primers, and a second sequence variation effective to substantially eliminate the production of sequencing products from interaction of the internal quantitation standard with the first sequencing. In kits for evaluation of genes with multiple regions of interest, the kit may further contain one or more additional pairs of amplification primers for amplifying the additional regions of interest, and one or more additional sequencing primers for sequencing the additional amplification products. It will be appreciated that these reagents will generally be packaged separately in the kit to provide maximum versatility in setting the amount of the IQS added to the sample and combining the IQS with the sample in advance of the addition of amplification primers, however, combinations in which the IQS was combined in advance with each type of amplification primer pair in the kit would not be outside the scope of this invention. The kit of the invention may further include additional reagents such as polymerase enzymes, buffers, and deoxy and dideoxynucleotide triphosphates as appropriate to the amplification and sequencing reactions to be performed.

The invention will now be further exemplified with reference to the following, non-limiting examples.

EXAMPLE 1

A synthetic nucleic acid segment for the IQS was constructed by performing PCR-based site directed mutagenesis of a sequence derived from the reverse transcriptase (RT) gene of HIV-1 wild-type strain HXB2 [Seq. ID No. 1]. The procedure used for producing the construct was similar to methods described by Silver et al. for PCR based site-directed mutagenesis (Silver et al. 1995, PCR Stratagies). Mutagenic PCR primers, RT558-INS-F [Seq. ID No.2] and RT964-MUT-R [Seq. ID No.3], were designed and synthesized for amplification of HIV-1 RT gene sequences from the plasmid pBKBH10S (FIG. 4), and incorporation of the necessary modifications required for the QS sequence (FIGS. 5 and 6). pKkbH10S was obtained through the AIDS Research Reagent Program, Division of AIDS, NIAID, NIH: pBKBH10S from Dr. John Rossi.

PCR was performed in 10 mM Tris-HCl (pH8.3), 50 mM KCl, 2.5 mM $MgCl_2$, 50 mM each dNTP (dATP, dCTP, dGTP, dTTP), 0.3 mM each of primer RT558-INS-F and RT964-MUT-R, 1 U Taq DNA polymerase (Roche Molecular Systems, Inc.), and $10^4$ copies of pBKBH10S in a total volume of 100 ml. Thermal cycling conditions were 94° C. for 2 minutes, followed by 25 cycles of 94° C. for 30 seconds, 60° C. for 30 seconds, and 72° C. for 1 minute. 100 ml of the PCR reaction was run on a 0.8% agarose gel. The gel was analysed via ethidium bromide staining and U.V. irradiation. The band of interest, a 419 bp fragment, was excised and purified using a commercially available PCR purification kit (Qiagen, Inc.). The purified PCR product was reamplified using the same PCR conditions stated except using the primers RT558F [Seq. ID No.4] and RT964-2-R [Seq. ID No.5] to incorporate the full RT-PCR primer binding sequences. The 448 bp amplifed fragment of interest was agarose gel purified using the same stated protocol and subcloned into a pGEM-T vector (Promega) to produce the pQSRTB plasmid.

The orientation of the IQS sequence in pQSRTB was such that transcription utilizing the plasmid's T7 promotor would produce sense strand HIV-1 sequence. 5 mg of pQSRTB was linearized by digestion with Not I restriction enzyme (Boehringer Mannheim). The linearized plasmid was treated for RNase contamination by incubation with Proteinase K followed by phenol:chloroform:isoamyl alcohol (25:24:1, respectively) extraction, Sodium Acetate/Ethanol precipitation, and resuspension in ddH2O to a concentraion of 0.25 mg/ml. An in vitro T7 polymerase transcription assay was performed using a commercially available kit (Ambion, Inc.) according to the manufacturer's protocol. cRNA transcripts from pQSRTB were extracted with phenol:chloroform:isoamyl alcohol (25:24:1), and precipitated with ammonium acetate, carrier t-RNA, and isopropanol. The QSRTB cRNA was resuspended in 100 ml of ddH2O.

EXAMPLE 2

Quantification of QSRTB cRNA Transcripts

The QSRTB cRNA was serially diluted 10-fold up to $10^{-16}$ fold. 10 ml of each serial dilution was amplified by RT-PCR in a buffer containing 50 mM Bicine-KOH (pH8.3), 100 mM potassium acetate, 2 mM manganese acetate, 200 mM each dNTP (dATP, dCTP, dGTP, dTTP), 0.2 mM each of primer RT558F and RT964-2-R, 4 U of rTth DNA polymerase and 250 copies of a control HIV-1 RNA molecule in a final volume of 100 ml. Thermal cycling conditions were 60° C. for 30 minutes, 93° C. for 1 minute, followed by 32 cycles of 93° C. for 15 seconds, and 60° C. for 1 minute. After thermal cycling, 5 ml of each RT-PCR sample were mixed 1:1 with formamide dye and 2 ml of each mixture was analysed on a MICROGENE CLIPPER sequencer and displayed using GENEOBJECTS sequence analysis software. Peak areas generated by the control HIV-1 and IQS fragments were qualitatively compared to determine an appropriate factor for diluting the concentrated stock of QSRTB cRNA.

After fragment analysis, the QSRTB cRNA stock was serially diluted by a factor of $2.5 \times 10^{-10}$. The diluted stock was quantified by quantitative competitive RT-PCR. RT-PCR was performed as stated except with 800 copies of an HIV-1 CRNA transcript (previously transcribed and quantified from the pBKBH10S plasmid) and 10 ml of the $2.5 \times 10^{-10}$ diluted QSRTB cRNA stock. 16 identical reactions were performed. After thermal cycling, the RT-PCR samples were analysed on a MicroGene CLIPPER sequencer and displayed using GENEOBJECTS analysis software. The QSRTB copy number per ml was extrapolated by averaging the ratios of fluorescence from the cyanine dye cy5.5 generated by the HIV-1 and QSRTB RT-PCR products and correlating the ratio of HIV-1 to QSRTB RT-PCR products to the initial amounts of HIV-1 and QSRTB cRNA per RT-PCR reaction. The QSRTB cRNA copy number was calculated to be 98 copies/ml for the $2.5 \times 10^{-10}$ diluted stock.

EXAMPLE 3

Amplification of a Sample Nucleic Acid for Quantification and Genotyping cRNA was prepared, using methods previously stated for synthetic RNA preparation, from a plasmid pMUT201 containing a cloned sequence of the HIV-1 reverse transcriptase gene derived from a drug resistant HIV-1 strain labelled as #201. The cRNA stock was serially diluted to a low copy number. A 10 ml aliquot of the mutant #201 HIV-1 cRNA was co-amplified with 980 copies of QSRTB quantitative standard cRNA using the 8RT-PCR method previously stated. A control RT-PCR reaction was performed that contained only 980 copies of QSRTB quantitative standard cRNA.

EXAMPLE 4

Quantification of the Sample Nucleic Acid

The products from the amplification reactions in Example 3 were analysed on a MICROGENE CLIPPER sequencer and analysed using GENEOBJECTS analysis software. Quantification of the initial mutant #201 cRNA sample was performed as previously stated. The relative fluorescence from the cyanine dye cy5.5 generated by HIV-1 mutant #201 and QSRTB RT-PCR products was measured using GENEOBJECTS analysis software. The initial amount of mutant #201 HIV-1 sample RNA in the RT-PCR was calculated by dividing the integrated peak area generated by the mutant HIV-1 sample fragment by the peak area generated by the QSRTB fragment and multiplying the result by initial copy number of QSRTB cRNA. The initial amount of HIV-1 mutant #201 RNA in the sample amplified was calculated to be 91 copies. The amplification reaction in Example 3 containing only QSRTB RNA produced only a single fragment, indicating the presence of only QSRTB control fragments and the absence of any HIV-1 sample derived fragments in the control reaction.

EXAMPLE 5

Genotypic Analysis of the Sample Nucleic Acid.

Aliquots of the RT-PCR reactions in (C) were sequenced using the CLIPä sequencing method in a buffer containing 20 mM Tris-HCl (pH 8.3), 2.5 mM magnesium chloride, 3 U Amplitaq FS DNA polymerase (Roche Molecular Systems, Inc.), 200 nM RT562F-A cy5.5 primer [Seq. ID No. 6], 200 nm RT595R cy5.0 primer [Seq. ID No. 7], and 375 mM dNTPs in four seperate reactions containing either 1.25 mM of either dideoxy-ATP, dideoxy-CTP, dideoxy-GTP, or dideoxy-TTP chain terminating nucleotides. Thermal cycling conditions were 5 minutes at 94° C. followed by 30 cycles of 94° C. for 20 seconds, 56° C. for 20 seconds and 70° C. for 1 minute 30 seconds, followed by a final extension step of 70° C. for 5 minutes. After thermal cycling, 14 ml of a formamide stop dye was added to the sequencing reaction mixture and sequencing products were denatured by incubation at 94° C. for 1 minute. The sequencing fragments labelled with both cy5.5 and cy5.0 cyanine dyes were analysed on a MICROGENE CLIPPER sequencer and displayed with GENEOBJECTS analysis software. Sequence data was analysed using GENELIBRARIAN analysis software and HIV-1 database.

Sequence data derived from the amplification reaction (C) containing mutant #201 HIV-1 and QSRTB fragments produced sequence data corresponding only to the mutant #201 HIV-1 RNA sequence, indicating that only sample RNA and not the quantitative standard QSRTB, whose sequence corresponds to a wild-type drug sensitive strain, was sequenced. Sequence data derived from the amplification control reaction containing only QSRTB fragments produced no sequencing data, indicating (i) the absence of HIV-1 sample derived fragments in the control amplification reaction; (ii) the inability of the sequencing primers used to produce qualitative sequence from the QSRTB quantitative standard.

EXAMPLE 6

Figure 7:
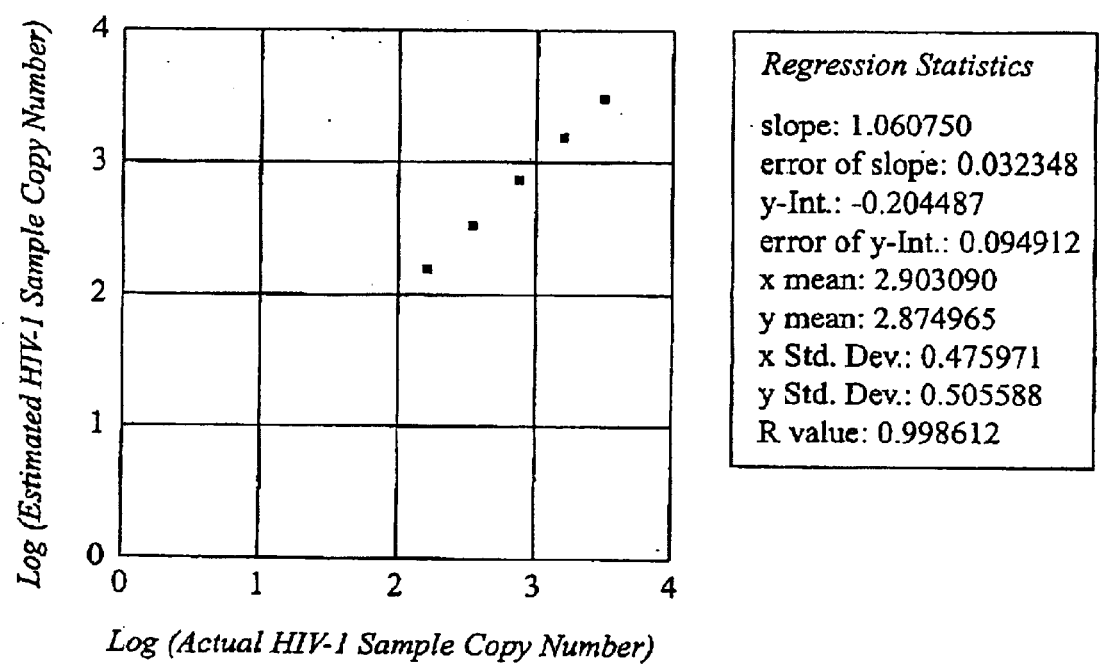
FIG. 7 shows the ability to quantify amounts of a nucleic acid target using the method of the invention.

To further demonstrate the ability of the method to quantify a nucleic acid target, pBKBH10S derived HIV-1 cRNA was serially diluted 2-fold such that 10 μl aliquots contained either 3200, 1600, 800, 400 or 200 copies of the HIV-1 cRNA. RT-PCR was performed as previously stated, expect with 980 copies of the QSRTB internal quantitation standard and either 3200, 1600, 800, 400 or 200 copies of the HIV-1 cRNA. The products of the RT-PCR amplification reaction were analyzed on a MICROGENE CLIPPER™ sequencer and data was displayed using GENEOBJECTS™ software. Quantification of the initial amount of HIV-1 cRNA was performed by comparing the relative CY5.5 fluorescence (measured as the area of the peak) generated by the HIV-1 cRNA and the QSRTB RT-PCR products for each sample and correlating the ration of RT-PCR products to the initial amount of RNA added to the RT-PCR reaction. A logarithmic graph of the estimated versus actual HIV-1 cRNA copy number was produced (FIG. 7). The graph is substantially linear, demonstrating the assay's ability to quantify a nucleic acid target.

What is claimed is:

1. A method for quantitative and qualitative analysis of a nucleic acid analyte in a sample suspected to contain the nucleic acid analyte, comprising the steps of:
   (a) preparing a reaction mixture containing the sample and a known amount of an internal quantitative standard;
   (b) combining a first aliquot of the reaction mixture with a set of amplification reagents, said reagents including a first primer pair which is effective to amplify a first region of the nucleic acid analyte if present in the sample to produce a first amplified sample fragment and to amplify at least a portion of the internal quantitation standard to produce a control fragment;
   (c) amplifying the nucleic acid analyte and the internal quantitation standard in the reaction mixture using the first primer pair to produce an amplification product mixture containing first amplified sample fragments and control fragments when the nucleic acid analyte is present in the sample, and only control fragments when the nucleic acid analyte is not present in the sample;
   (d) analyzing the relative amounts of first amplified sample fragments and control fragments in the amplification product mixture to quantify the amount of nucleic acid analyte in the sample; and
   (e) determining the sequence of the first amplified sample fragments in the amplification mixture to determine the qualitative characteristics of any nucleic acid analyte in the sample using at least a first sequencing primer, wherein the internal quantification fragment is derived from the analyte nucleic acid by the incorporation of a plurality of sequence variations, including at least a first sequence variation effective to render the internal quantitation standard distinguishable from the first amplified sample fragment, and a second sequence variation effective to substantially eliminate the production of sequencing products from interaction of the internal quantitation standard and the first sequencing primer.

2. The method according to claim 1, wherein the nucleic acid analyte includes a plurality of regions of interest, and wherein the first primer pair is effective to amplify only one of these regions.

3. The method according to claim 2, further comprising the step of combining one or more additional aliquots of the reaction mixture with one or more additional sets of amplification reagents, each additional set of reagents including an additional primer pair which is effective to amplify a further one of the regions of interest in the nucleic acid analyte if it is present in the sample to produce an additional amplified sample fragment, wherein the additional primers in the additional reagent sets are not effective to amplify the internal quantitation standard.

4. The method according to claim 1, wherein the nucleic acid analyte is HIV-1.

5. The method according to claim 4, wherein the HIV-1 nucleic acid analyte is evaluated by analysis of the protease gene, and a beginning, middle and end portion of the reverse transcriptase gene as separate regions of interest, and wherein the first primer pair is effective to amplify only one of these regions.

6. The method according to claim 5, wherein the first primer pair is effective to amplify the beginning portion of the reverse transcriptase gene of HIV-1.

7. The method according to claim 6, further comprising the step of combining three additional aliquots of the reaction mixture with three additional sets of amplification reagents, each additional set of reagents including an additional primer pair which is effective to amplify one of the protease gene, or the middle or end portion of the reverse transcriptase in the HIV-1 nucleic acid analyte if it is present in the sample to produce three amplification product mixtures, each containing an additional amplified sample fragment, wherein the additional primers in the additional reagent sets are not effective to amplify the internal quantitation standard.

8. The method of claim 7, wherein the first sequence variation in the internal quantitation standard is an insertion or deletion mutation in the beginning portion of the HIV-1 gene.

9. The method of claim 6, wherein the first sequence variation in the internal quantitation standard is an insertion or deletion mutation in the beginning portion of the HIV-1 gene.

10. An internal quantification standard for use for analysis of an analyte nucleic acid comprising a nucleic acid polymer derived from the analyte nucleic acid by the incorporation of a plurality of sequence variations, including at least a first sequence variation effective to render a control fragment produced by amplification of the internal quantitation standard with a first pair of primers distinguishable from a first amplified sample fragment produced by amplification of the analyte nucleic acid with the first pair of primers, and a second sequence variation effective to substantially eliminate the production of sequencing products from interaction of the internal quantitation standard with a sequencing primer, said sequencing primer being effective for producing sequencing fragments from the first amplified sample fragment.

11. The internal quantitation standard of claim 10, wherein the first sequence variation is an insertion or deletion mutation.

12. The internal quantitation standard of claim 11, wherein the analyte nucleic acid from which the internal quantitation standard is derived comprises the protease and reverse transcriptase genes of HIV-1.

13. The internal quantitation standard of claim 12, wherein the first sequence variation is an insertion or deletion mutation.

14. A kit for quantitative and qualitative analysis of a nucleic acid analyte in a sample comprising, in packaged combination:
   (a) a first pair of amplification primers effective to amplify a first region of the nucleic acid analyte to produce a first amplification product;
   (b) a first sequencing primer for generating sequencing fragments from the first amplification; and
   (c) an internal quantitation standard, comprising a nucleic acid polymer derived from the analyte nucleic acid by the incorporation of a plurality of sequence variations, including at least a first sequence variation effective to render a control fragment produced by amplification of the internal quantitation standard with the first pair of primers distinguishable from a first amplified sample fragment produced by amplification of the analyte nucleic acid with the first pair of primers, and a second sequence variation effective to substantially eliminate the production of sequencing products from interaction of the internal quantitation standard with the first sequencing primer, said sequencing primer being effective for producing sequencing fragments from the first amplified sample fragment.

15. The kit of claim 14, further comprising a second pair of amplification primers effective to produce a second amplification product from a second region of the nucleic acid analyte different from the first region, and a second sequencing primer for generating sequencing fragments from the second amplification product.

16. The kit of claim 15, wherein the nucleic acid analyte is HIV-1, and the first and second regions are selected from among regions spanning areas of sequence variability in the protease gene and regions spanning areas of sequence variability in the reverse transcriptase gene.

17. The kit of claim 14, wherein the first sequence variation is an insertion or deletion mutation.

18. The kit of claim 17, wherein the nucleic acid analyte is HIV-1, and the first and second regions are selected from among regions spanning areas of sequence variability in the protease gene and regions spanning areas of sequence variability in the reverse transcriptase gene.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 433
        (B) TYPE: nucleic acid
        (C) STRANDEDNESS: double
        (D) TOPOLOGY: linear (ii) MOLECULE TYPE: genomic RNA (iii) HYPOTHETICAL: no (iv) ANTI-SENSE: no (v) FRAGMENT TYPE: internal (vi) ORIGINAL SOURCE:
        (A) ORGANISM: HIV-1

(xi) SEQUENCE DESCRIPTION: SEQ ID NO: 1:

```
AAAAGTTAAA CAATGGCCAT TGACAGAAGA AAAAATAAAA GCATTAGTAG          50

AAATTTGTAC AGAGATGGAA AAGGAAGGGA AAATTTCAAA AATTGGGCCT         100

GAAAATCCAT ACAATACTCC AGTATTTGCC ATAAAGAAAA AAGACAGTAC         150

TAAATGGAGA AAATTAGTAG ATTTCAGAGA ACTTAATAAG AGAACTCAAG         200

ACTTCTGGGA AGTTCAATTA GGAATACCAC ATCCCGCAGG GTTAAAAAAG         250
```

-continued

| | |
|---|---|
| AAAAAATCAG TAACAGTACT GGATGTGGGT GATGCATATT TTTCAGTTCC | 300 |
| CTTAGATGAA GACTTCAGGA AGTATACTGC ATTTACCATA CCTAGTATAA | 350 |
| ACAATGAGAC ACCAGGGATT AGATATCAGT ACAATGTGCT TCCACAGGGA | 400 |
| TGGAAAGGAT CACCAGCAAT ATTCCAAAGT AGC | 433 |

(2) INFORMATION FOR SEQ ID NO: 2:

(i) SEQUENCE CHARACTERISTICS:
        (A) LENGTH: 56
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 2:

| | |
|---|---|
| GGCCATTGAC AGTCCTAAAT AAATAGCAAA GAAAAAATAA AAGCATTAGT AGAAAT | 56 |

(2) INFORMATION FOR SEQ ID NO: 3:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 3:

| | |
|---|---|
| TGCTGGTGAT CCTTTGGATC CCTGTGGAAG | 30 |

(2) INFORMATION FOR SEQ ID NO: 4:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 4:

```
AAAAGTTAAA CAATGGCCAT TGACAG                                              26

(2) INFORMATION FOR SEQ ID NO: 5:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 5:

GCTACTTTGG AATATTGCTG GTGATCC                                             27

(2) INFORMATION FOR SEQ ID NO: 6:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 6:

GTTAAACAAT GGCCATTGAC AGAAGA                                              26

(2) INFORMATION FOR SEQ ID NO: 7:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (v) FRAGMENT TYPE: internal (vi) ORIGINAL SOURCE:
        (A) ORGANISM: HIV-1

(xi) SEQUENCE DESCRIPTION: SEQ ID NO: 7:

GGAATATTGC TGGTGATCCT TTCC                                                24
```